(12) United States Patent
Koch

(10) Patent No.: US 6,590,954 B1
(45) Date of Patent: Jul. 8, 2003

(54) X-RAY SHEARING INTERFEROMETER

(75) Inventor: Jeffrey A. Koch, Livermore, CA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 10/177,402

(22) Filed: Jun. 20, 2002

Related U.S. Application Data

(60) Provisional application No. 60/300,413, filed on Jun. 20, 2001.

(51) Int. Cl.[7] .................................................. G03H 5/00
(52) U.S. Cl. ...................................................... 378/36
(58) Field of Search ........................................... 378/36

(56) References Cited

U.S. PATENT DOCUMENTS 6,195,410 B1 * 2/2001 Cash .......................... 378/36

* cited by examiner

Primary Examiner—Craig E. Church
(74) Attorney, Agent, or Firm—William C. Daubenspeck; Paul A. Gottlieb

(57) ABSTRACT

An x-ray interferometer for analyzing high density plasmas and optically opaque materials includes a point-like x-ray source for providing a broadband x-ray source. The x-rays are directed through a target material and then are reflected by a high-quality ellipsoidally-bent imaging crystal to a diffraction grating disposed at 1× magnification. A spherically-bent imaging crystal is employed when the x-rays that are incident on the crystal surface are normal to that surface. The diffraction grating produces multiple beams which interfere with one another to produce an interference pattern which contains information about the target. A detector is disposed at the position of the image of the target produced by the interfering beams.

5 Claims, 4 Drawing Sheets

Point Source, monochromatic

Point Source, E/ΔE = 25,000

5 μm backlight, monochromatic

X-RAY SHEARING INTERFEROMETER

CROSS-REFERENCE TO RELATED APPLICATIONS

This Application claims priority from Provisional Patent Application Ser. No. 60/300,413, filed Jun. 20, 2001. The entire contents of such Provisional Patent Application are hereby incorporated herein by reference.

The United States Government has rights in this invention pursuant to Contract No. W-7405-ENG48 between the United States Department of Energy and the University of California for the operation of the Lawrence Livermore National Laboratory.

BACKGROUND OF THE INVENTION

1. Field of the Invention

This invention relates in general to the field of x-ray optics and x-ray imaging and, in particular, to an x-ray interferometer useful for analyzing high density plasmas and optically opaque materials.

2. Description of the Problem

Diagnosis of plasma density and density variations is difficult when densities are high because high-density plasmas absorb most electromagnetic radiation. Density diagnosis by visible-light interferometry is therefore impossible for many types of experiments including inertial-confinement fusion (ICF) and ultra-high-irradiance plasma studies.

Possible areas where X-ray interferometry could be a useful diagnostic include: side-on and face-on radiography to measure density variations well above critical density such as shocked, cold, near-solid-p plasmas and USP laser irradiated solids; measurements of plasma formation near hohlraum walls a sub-critical densities to complement existing data; and measurements of ICF implosion density.

A related problem area is the diagnosis of opaque ICF beryllium shell targets containing cryogenic hydrogen ice. This ice layer must be extremely smooth, and characterization is made extremely difficult or impossible when the shell surrounding the ice is not transparent to visible light. One possible solution is x-ray interferometry, but the difficulty is utilizing relatively incoherent x-ray sources and controlling vibrations.

High-energy x-rays can penetrate these plasmas, but optical systems are difficult to fabricate, and path lengths must be extremely well matched in order to produce interference effects which relate to density. X-ray interferometers using reference beam paths have been produced, but are not suitable for laser-produced plasma experiments.

X-ray interferometry is difficult for several reasons. Optical path differences (OPDs) are small at low densities and at short wavelengths, which would imply that long wavelengths would perform better. For 2 keV photons for example, there is only an approximately eight wave phase difference for a 100 $\mu$m path length through a vacuum compared to a similar path through a near-solid-$\rho$plasma target. However, adsorption is large at high densities and long wave lengths. In addition, longitudinal coherence lengths are small for x-rays, making path length matching challenging. Requirements for spatial coherence, backlight brightness, useable time resolution and target-plasma self-emission limits can also be stringent.

SUMMARY OF THE INVENTION

It is therefore an object of the present invention to allow application of optical techniques to x-ray interferometry.

Another object of the present invention is to provide x-ray interferometry imaging having matched path lengths for all rays to the $4^{th}$ order in the light-path function.

Another object of the present invention is to provide x-ray interferometry having high-resolution imaging that allows fine-scale features to be probed.

A further object of the present invention is to provide X-ray interferometry having high monochromaticity.

Another object of the present invention is to provide X-ray interferometry wherein rocking-curve width is large near normal incidence.

These and other object are provided In the shearing interferometer of the present invention by using wavefronts created by a high-quality spherically-bent imaging crystal operating near normal incidence. A target is back-illuminated by a point-like x-ray source and the spherically-bent imaging crystal provides equal optical path lengths to one or more diffraction gratings acting as x-ray beam splitters. The split beams are analyzed to determine optical path length or phase differences between beams following different trajectories through the target. The spherically-bent imaging crystal enables broad-bandwidth x-ray sources to be utilized. The diffraction grating provides efficient x-ray beam splitting. And the common-path arrangement minimizes susceptibility to vibrations for static measurements.

The advantages and features of the present invention may be better understood from the following detailed description in conjunction with the accompanying drawing wherein:

DESCRIPTION OF THE PREFERRED EMBODIMENT

Figure 1:
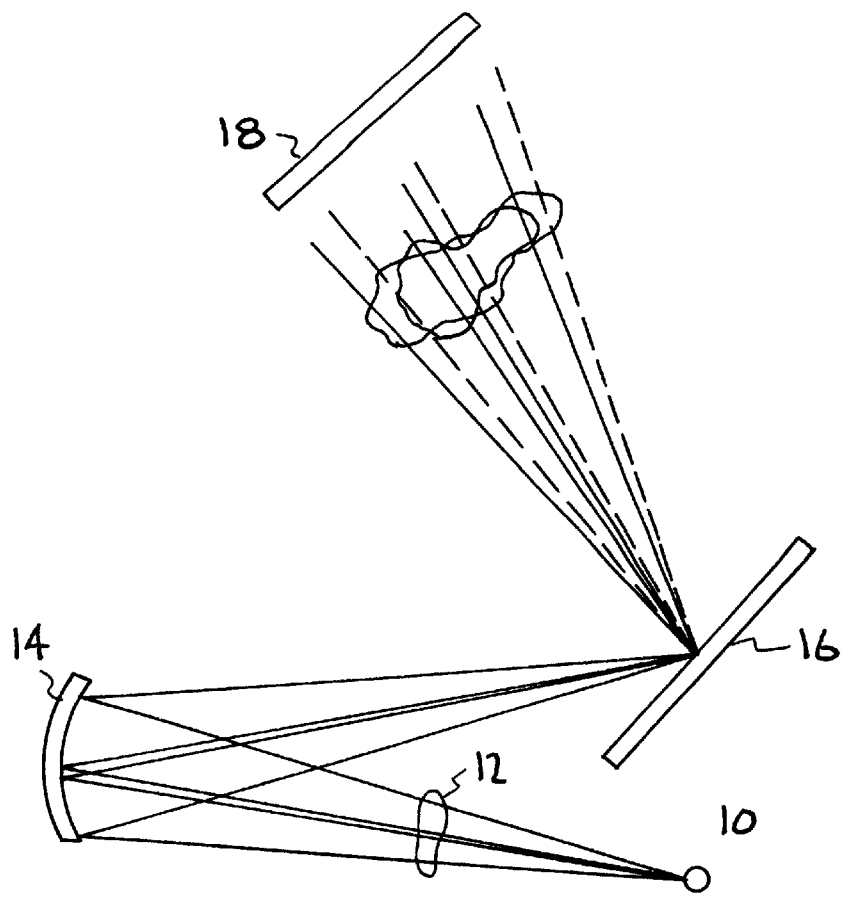
FIG. 1 is a schematic drawing illustrating the x-ray shearing interferometer of the present invention.

Referring now FIG. 1, x-rays are emitted from a point-like source 10 and back-illuminate a target 12 such as plasma. The point-like source 10 may be a conventional broadband laser-generated x-ray source directed through a pin-hole. The x-rays that are transmitted though the target 12 are reflected by a high-quality spherically-bent imaging crystal 14. The spherically-bent imaging crystal 14 focuses the transmitted x-rays back down to a point-like image of the x-ray source at 1x magnification. A diffraction grating means 16, operating in either transmission or reflection (reflection is shown in FIG. 1), is disposed at the point-like image of the x-ray source. The grating means 16, which may include one or more gratings, produces multiple beams which interfere with one another to produce an interference pattern which contains information about the optical path variations through the target 12. The x-ray beams then diverge and fall onto a detector 18. The detector 18 is placed at the position of the image of the target, which is imaged with magnification greater the one.

The narrow reflective bandwidth of the spherically-bent imaging crystal 14 limits the range of x-ray wavelengths from the broadband x-ray source 10 that are reflected to the grating means 16, and, therefore provides a measure of longitudinal coherence. A high-quality spherically-bent crystal means a crystal that is perfectly spherical to within the longitudinal coherence of the reflected x-rays. The imaging properties of the crystal 14 ensure that the x-rays that are refracted by the target 12 fall onto the image of the target where the detector 18 is disposed. The 1× magnification of the x-ray source 10 onto the grating means 16 ensures that the very highest matching of path lengths for different rays is obtained. The grating means 16 serves as a beamsplitter for recombining rays following different trajectories through the target 12 and can operate at x-ray wavelengths in transmission or in reflection at grazing angles of incidence.

It is noted that a spherical crystal will provide best matching path lengths when the x-rays that are incident on the crystal surface are substantially normal to that surface. If for some reason, the x-rays are desired to or required to strike the crystal surface from a direction off-set from normal to the surface, the curvature of the crystal surface which best provides matching path lengths for different rays may not be a spherical curvature. A different ellipsoidal surface may best provide matching path lengths.

The grating means 16 should ideally produce variable shearing of the wavefronts, and should interfere beams with comparable intensity levels. A first approach is to use a multi-frequency grating to produce two sets of overlapping orders. In this case, interference is between two first-order diffracted beams. However, the shear is not variable. This type of grating is illustrated by Wyant, "Double Frequency Grating Lateral Shear Interferometer", Appl. Opt 12, 2057 (1973).

Figure 2A:
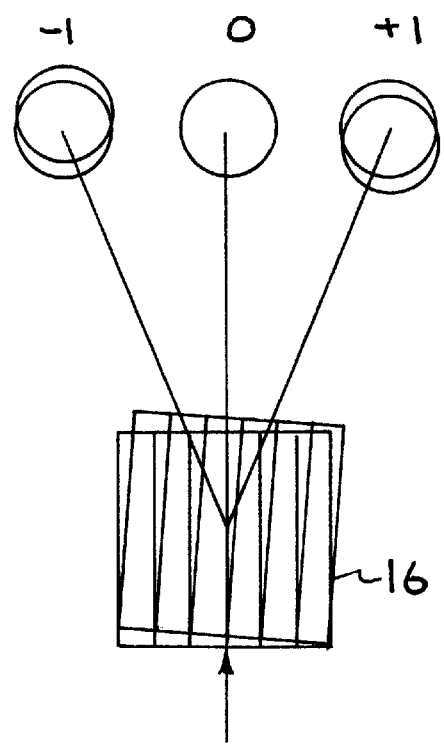
FIGS. 2*a* and 2*b* illustrate dual transmission (crossed) gratings with a slight tilt between them for producing lateral shear in a single direction and in orthogonal directions, respectively.
Figure 2B:
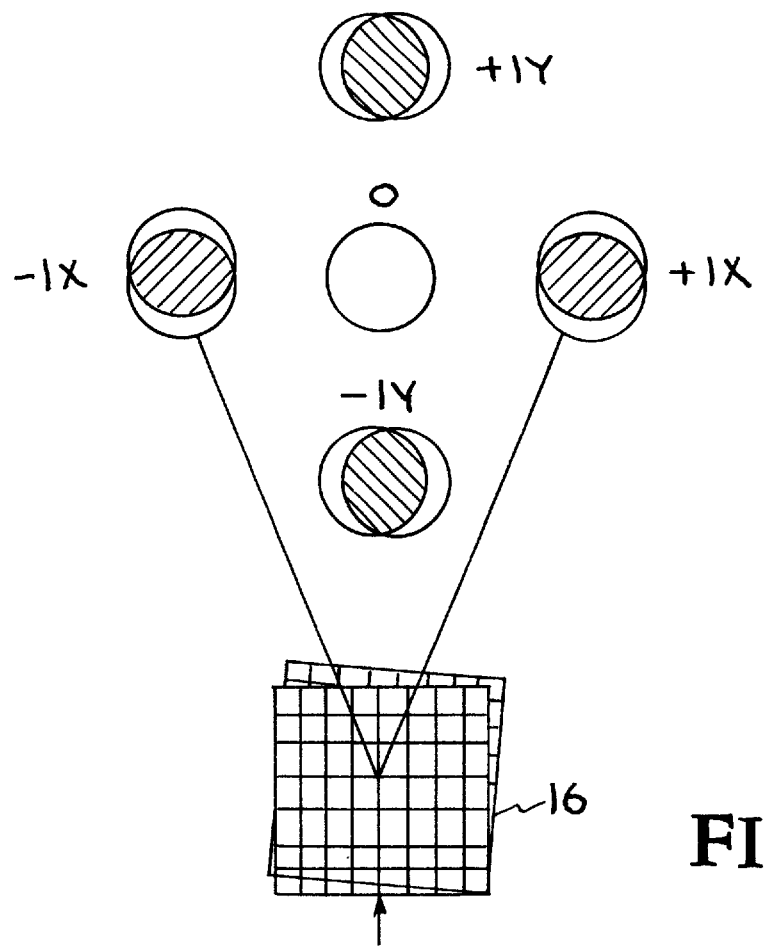

Another approach is to use two single-frequency diffraction gratings which are crossed with respect to one another as illustrated in FIGS. 2a and 2b. In this second approach, interference is between two first-order diffracted beams and the shear is variable by changing the cross-angle between the gratings. The use of dual transmission gratings with a slight tilt between them provides continuously variable shear at the cost of reduced efficiency compared with the best blazed reflection gratings (though phase gratings are possible as well). This approach is illustrated by Rimmer and Wyant, Appl. Opt. 14, 142 (1975). Shear in the perpendicular direction could be obtained simultaneously using square-array gratings as illustrated in FIG. 2b.

Figure 3:
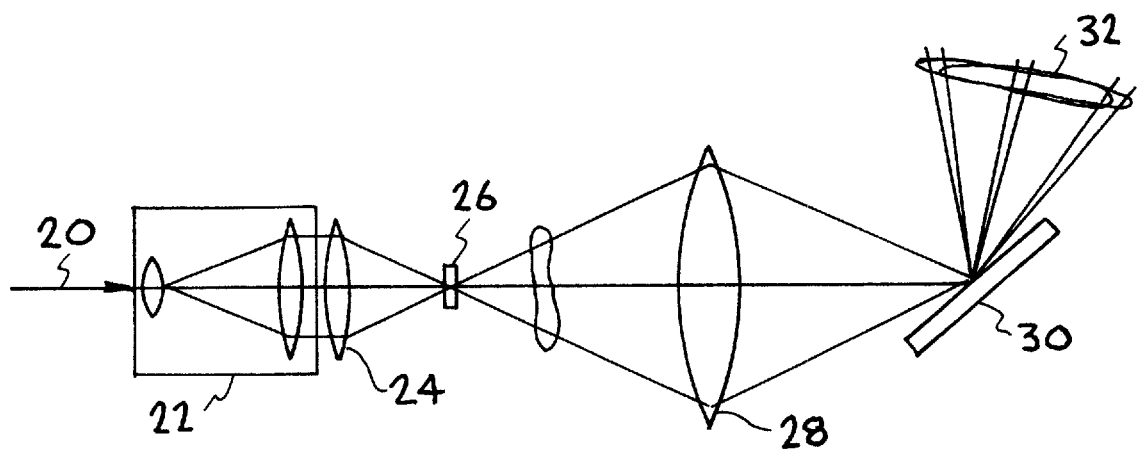
FIG. 3 is a schematic drawing illustrating a visible-light interferometer used to investigate the concept of the present invention.

FIG. 3 shows a visible light interferometer constructed to explore the concept of the present invention. A laser beam 20 was directed through an expander 22 and focused by lens 24 though a diffuser 26 to create a small incoherent source. After passing through the diffuser 26, the expanding laser beam is directed through a test object to an imaging lens 28 that serves the purpose of the spherical crystal in the invention. The imaging lens 28 images the expanded laser beam onto a grating 30 which forms test images 32. The test system produced clear fringes of a transmissive aberrator (plastic or glass window).

Figure 4:
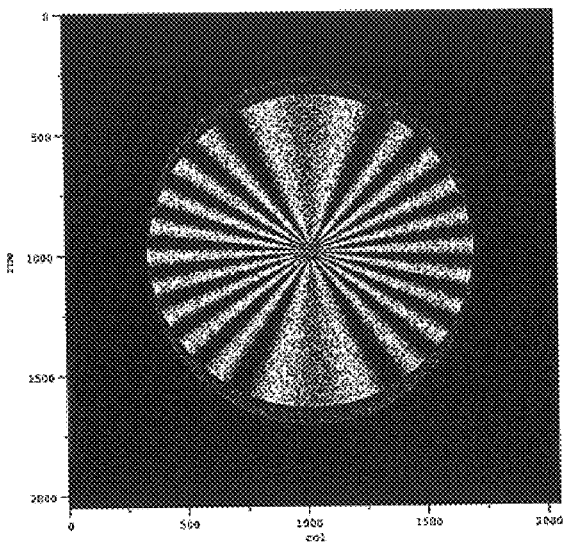
FIGS. 4–6 illustrate the results of computer simulation of the present invention illustrating its operation.
Figure 5:
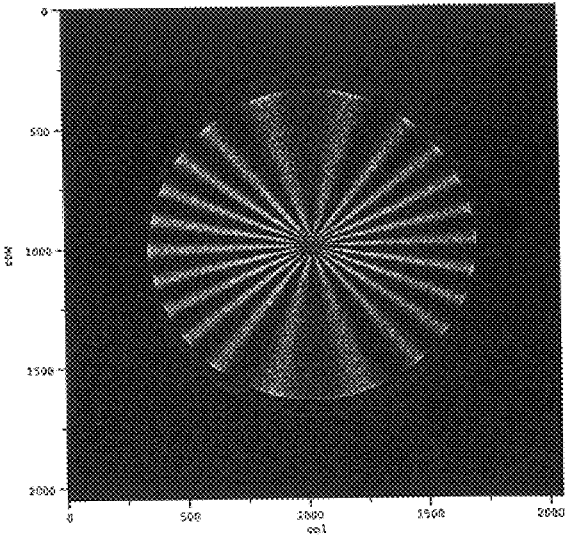
Figure 6:
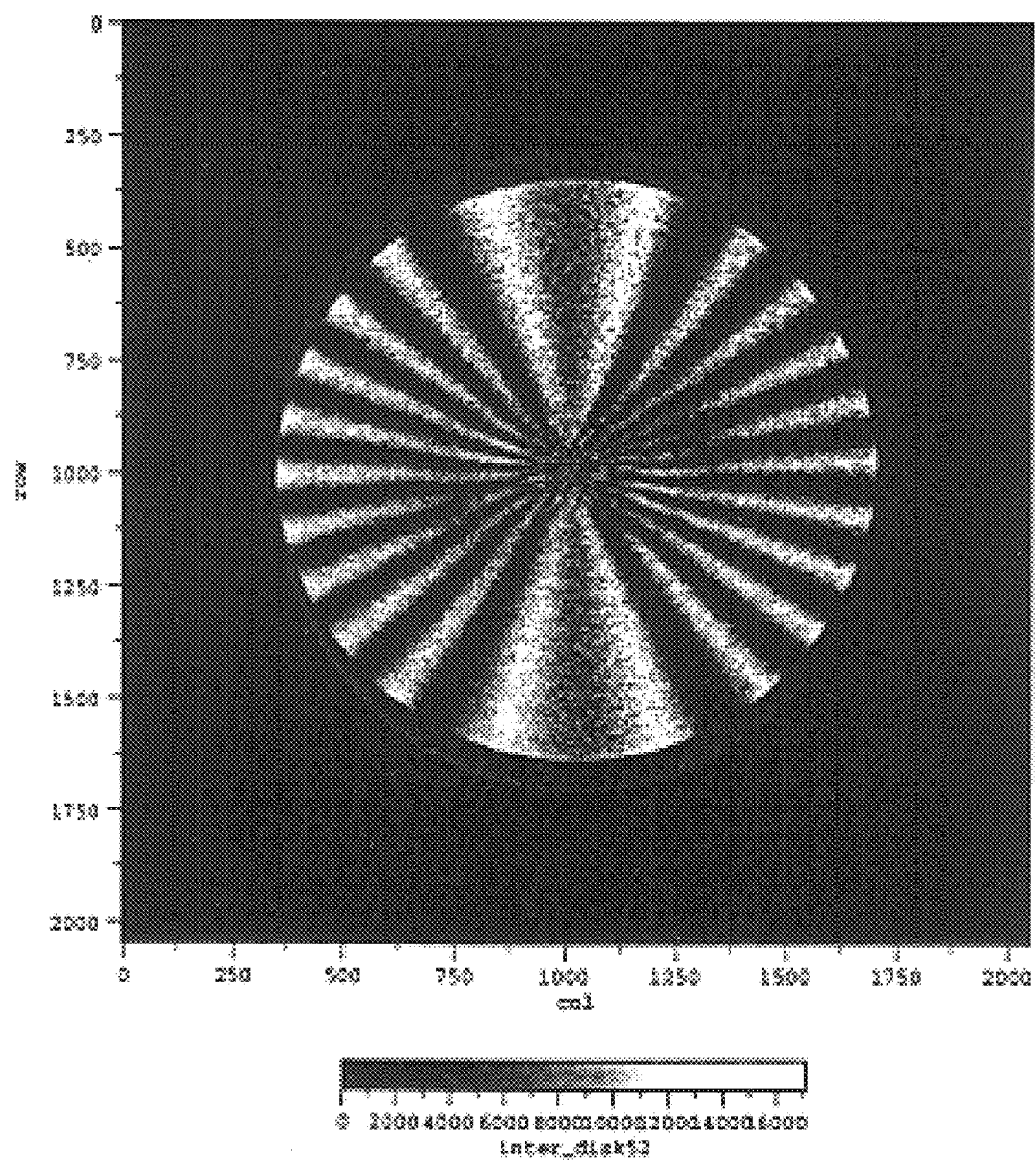

FIGS. 4–6 illustrate the results of a computer simulation of the invention assuming a conical wavefront, 100 waves peak-to-valley and vertical shearing. FIG. 4 shows the diffraction order produced by a monochromatic point source. FIG. 5 shows the diffraction order produced by point source having a finite bandwidth $E/\Delta E=25{,}000$ and illustrates that crystal bandwidth is adequate for operation of the invention. FIG. 6 shows the diffraction order produced by a 5 $\mu$m monochromatic source and illustrates that a finite 5 $\mu$m monochromatic source is also adequate for operation of the invention.

The invention claimed is:

1. An x-ray interferometer for analyzing a target comprising:

a point-like x-ray source for back-illuminating said target;

an ellipsoidally-bent imaging crystal for receiving said x-rays after traversing said target and focusing said x-rays to an image of the x-ray source;

diffraction grating means disposed at the image of the source, said grating producing at least two x-ray beams which interfere with one another; and detector means disposed in the path of said interfering x-ray beams to provide an image of the target.

2. The x-ray interferometer as recited in claim 1 wherein said grating means comprises a multiple frequency diffraction grating for producing said interfering x-ray beams.

3. The x-ray interferometer as recited in claim 1 wherein said grating means comprises two single-frequency diffraction gratings which are disposed crossed with respect to one another for producing two interfering x-ray beams.

4. The x-ray interferometer as recited in claim 1 wherein said ellipsoidally-bent crystal is a spherically-bent crystal.

5. The x-ray interferometer as recited in claim 1 wherein said diffraction grating means is disposed at the 1× magnification location from the imaging crystal.

* * * * *